United States Patent
Mori et al.

(10) Patent No.: US 6,642,405 B1
(45) Date of Patent: Nov. 4, 2003

(54) METHOD FOR PRODUCING ACRYLONITRILE, CATALYST FOR USE THEREIN AND METHOD FOR PREPARING THE SAME

(75) Inventors: Kunio Mori, Yokohama (JP); Yutaka Sasaki, Kamakura (JP); Kenichi Miyaki, Yokohama (JP); Hirokazu Watanabe, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/089,079
(22) PCT Filed: Oct. 17, 2000
(86) PCT No.: PCT/JP00/07192
§ 371 (c)(1), (2), (4) Date: Apr. 10, 2002
(87) PCT Pub. No.: WO01/28984
PCT Pub. Date: Oct. 17, 2000

(30) Foreign Application Priority Data

Oct. 18, 1999 (JP) ............................................. 11-295915

(51) Int. Cl.[7] ............................................. C07C 253/00
(52) U.S. Cl. ....................................... 558/338; 502/205
(58) Field of Search ........................... 558/338; 502/205

(56) References Cited

U.S. PATENT DOCUMENTS 5,059,573 A * 10/1991 Sasaki et al. ............... 502/205
5,834,394 A    11/1998 Chen et al. .................. 502/302

FOREIGN PATENT DOCUMENTS

| JP | 7-48334 | 2/1995 |
| JP | 11-33400 | 2/1999 |
| WO | 99/54037 | 10/1999 |

* cited by examiner

Primary Examiner—Joseph K. McKane
Assistant Examiner—Rei Shiao
(74) Attorney, Agent, or Firm—Oblon, Spivak, McClelland, Maier & Neustadt, P.C.

(57) ABSTRACT

For the production of acrylonitrile by ammoxidation of propylene, there is provided a process capable of giving a high yield and maintaining such an effect for a long period of time.

In producing acrylonitrile by ammoxidation of propylene, a fluidized bed catalyst is used and the reaction is carried out while appropriately adding a molybdenum-containing material, wherein the fluidized bed catalyst contains molybdenum, bismuth, iron, nickel, chromium, potassium, an F component and silica as essential components, and has a number of Mo/Me of from 0.8 to 1, wherein the Mo/Me is a number obtained by dividing the product 20 of a valence number of molybdenum as molybdic acid and an atomic ratio of molybdenum by the sum of respective products of respective valence numbers and atomic ratios of bismuth, iron, nickel, chromium, potassium, the F component element, a G component element and a Y component element.

16 Claims, No Drawings

METHOD FOR PRODUCING ACRYLONITRILE, CATALYST FOR USE THEREIN AND METHOD FOR PREPARING THE SAME

TECHNICAL FIELD

The present invention relates to a catalyst suitably used for the production of acrylonitrile by ammoxidation of propylene, a process for producing said catalyst and a process for producing acrylonitrile by using said catalyst.

BACKGROUND ART

With respect to a catalyst suitably used for the production of acrylonitrile by ammoxidation of propylene, various catalysts are disclosed. In JP-B-38-17967, there is disclosed an oxide catalyst containing molybdenum, bismuth and iron, and in JP-B-38-19111, there is disclosed an oxide catalyst containing iron and antimony. After that, studies have been extensively continued to improve these catalysts. For example, in JP-B-51-33888, JP-B-55-56839, JP-B-58-2232, JP-B-61-26419, JP-A-7-47272, JP-A-10-43595, JP-A-4-11805 and the like, there are disclosed one improvement comprising using another component in addition to molybdenum, bismuth and iron, and the other improvement comprising using another component in addition to iron and antimony.

Also with respect to a process for producing a fluidized bed catalyst, there are descriptions in JP-B-37-8568, JP-B-42-22476, JP-B-57-49253, JP Patent 2640356, JP Patent 2701065, JP Patent 2747920 and others.

Further, in using these catalysts for the ammoxidation reaction, it is proposed to carry out said reaction while supplying a molybdenum-containing material thereto, thereby maintaining the catalyst efficiency. For example, in JP-B-58-57422, there is disclosed a process, wherein a particle formed by supporting a molybdenum-containing material on silica is supplied to a fluidized bed catalyst containing molybdenum, bismuth, iron, cobalt and others, thereby restoring the catalyst efficiency. In DE 3, 311, 521 and WO 97/33863, there is disclosed a process, wherein molybdenum trioxide or a molybdenum compound capable of converting to said trioxide in a specific amount is supplied to a catalyst similar to that mentioned above.

These catalysts of the prior arts were effective to improve a yield of acrylonitrile to a certain extent. However, these catalysts have been N still insufficient in respect to repeatability in the production thereof and long-term stability of the yield) of desired products. It has been very important to solve these problems from an industrial point of view and further improvements of these catalysts have been requested.

In addition, also with respect to the process comprising supplying the molybdenum component to maintain the catalyst efficiency, it is difficult to say that it is always effective. Even if the molybdenum component is supplied, no effect can be observed in the case where a catalyst structure is markedly damaged. Further, even if loss of molybdenum is not so large, no effect can be exhibited in the case where lowering of the catalyst efficiency is mainly caused by change of the catalyst structure. It is finding that the catalyst to be applied it self-should be stable and should have no extreme damage on its structure.

It has been desired to find a catalyst, which is capable of further improving the acrylonitrile yield, satisfactory in the repeatability in the production thereof, stable when used for the ammoxidation reaction, and capable of maintaining its efficiency for a long period of time by the supply of molybdenum. The present invention is to solve these problems and to improve Japanese Patent No. 2640356, Japanese Patent Application No. 10-128098 and others particularly with the aim of improving a process for producing acrylonitrile by ammoxidation of propylene.

DISCLOSURE OF INVENTION

The present inventors have undertaken extensive studies to solve the above-mentioned problems. As a result, it has been found that the desired product can be obtained with a high yield and such an effect can be maintained for a long period of time, when a fluidized bed catalyst is used and the ammoxidation reaction is carried out while appropriately adding and supplying a molybdenum-containing material, which fluidized bed catalyst comprises molybdenum, bismuth, iron, nickel, chromium, an F component of a trivalent metal and potassium as essential components and has an Mo/Me of from 0.8 to 1, wherein the Mo/Me is a number obtained by dividing the product 20 of a valence number of molybdenum as molybdic acid and an atomic ratio of molybdenum by the sum of respective products of respective valence numbers and atomic ratios of bismuth, iron, nickel, chromium, potassium, an F component element, a G component element and a Y component element.

The fluidized bed catalyst is capable of giving a high acrylonitrile yield. Moreover, the catalyst is stable in its catalyst structure, and so resistant to use of a long-term reaction. When the Mo/Me exceeds the above-defined range, an excess molybdenum component may enter the interface of metal molybdate, which functions as a catalyst, and as a result, dysfunction may be caused. Whereas, when the Mo/Me is less than the above-defined range, the acrylonitrile yield decreases and at the same time variation with the lapse of time becomes large.

Still, in the case where the catalyst in accordance with the present invention, which is structurally stable, is used without interruption for the ammoxidation reaction, a decrease of the acrylonitrile yield due to escaping of the molybdenum component may be observed. Since the ammoxidation reaction using this kind of the molybdenum containing catalyst is carried out at a temperature exceeding 400° C., it seems that the escaping of the molybdenum component is inevitable during the reaction. In this regard, the acrylonitrile yield was able to be maintained at a high degree for a long period of time by continuing the reaction while adding the molybdenum-containing material.

According to the catalyst in accordance with the present invention, which is structurally stable, the yield of desired products can be more sufficiently maintained, improved or restored by appropriately adding the molybdenum-containing material at the time of the ammoxidation reaction. Moreover, since the addition of the molybdenum-containing material at the time of the ammoxidation reaction can be repeated, the catalyst in accordance with the present invention can be used for a much longer period of time by such a repeated addition of the molybdenum-containing material. The addition of the molybdenum-containing material may be carried out from an early stage of the reaction. In applying the catalyst to the ammoxidation reaction, a catalyst surface composition and a catalyst structure are optimized by means of a preparation composition, a preparation method or the like. However, it is difficult to say that the optimization can be always realized. As the case may be, the yield of the desired product increases by the addition of the molybdenum-containing material at an early stage of the reaction. This seems that optimization of the catalyst surface composition and the structure thereof can be realized also with the aid of the addition of the molybdenum-containing material.

With respect to a conventional catalyst, the acrylonitrile yield has been insufficient, and it has not been always easy to maintain its efficiency even when the reaction is carried out while adding the molybdenum-containing material. Moreover, it has been insufficient to restore its efficiency even if the molybdenum-containing material is added on the ground that the yield decreases owing to a long-term use of the catalyst. According to the present invention, there is provided a process capable of maintaining a high acrylonitrile yield for a long period of time.

That is, the present invention provides a process for producing acrylonitrile, which comprises using a fluidized bed catalyst of a composition represented by the following empirical formula in the production of acrylonitrile by ammoxidation of propylene. The present invention also provides a process for producing acrylonitrile according to said process, wherein the ammoxidation reaction is carried out while appropriately adding a molybdenum-containing material.

$$Mo_{10} Bi_a Fe_b Sb_c Ni_d Cr_e F_f G_g H_h K_k M_m X_x Y_y O_i (SiO_2)_j$$

In the formula, Mo, Bi, Fe, Sb, Ni, Cr and K are molybdenum, bismuth, iron, antimony, nickel, chromium and potassium, respectively; F is at least one element selected from the group consisting of yttrium, lanthanum, cerium, praseodymium, neodymium, samarium, aluminum and gallium, in which group preferred are lanthanum, cerium, praseodymium, neodymium, samarium and aluminum, and more preferred are lanthanum and cerium; G is at least one element selected from the group consisting of magnesium, calcium, strontium, barium, manganese, cobalt, copper, zinc and cadmium, in which group preferred are magnesium, calcium, manganese, cobalt and zinc; H is at least one element selected from the group consisting of titanium, zirconium, vanadium, niobium, tantalum, tungsten, germanium, tin and lead, in which group preferred are zirconium, vanadium, niobium, tungsten and germanium; M is at least one element selected from the group consisting of ruthenium, rhodium, palladium, rhenium, osmium, iridium, platinum and silver, in which group preferred are ruthenium and palladium; X is at least one element selected from the group consisting of phosphorus, boron and tellurium; Y is at least one element selected from the group consisting of lithium, sodium, rubidium, cesium and thallium, in which group preferred are rubidium and cesium; O is oxygen; Si is silicon; and affixes a, b, c, d, e, f, g, h, k, x, y, i and j are independently of one another an atomic ratio, provided that a=0.2 to 1.5, preferably 0.3 to 1.2, more preferably 0.3 to 0.8, b=0.7 to 15, preferably 0.8 to 13, more preferably 1 to 8, c=0 to 20, preferably 0 to 15, more preferably 0 to 10, d=3 to 8, preferably 4 to 7, more preferably 4 to 6, e=0.1 to 2.5, preferably 0.2 to 2, more preferably 0.5 to 1.5, f=0.1 to 1.5, preferably 0.2 to 1, more preferably 0.4 to 0.8, g=0 to 5, preferably 0 to 3, more preferably 0 to 2, h=0 to 3, preferably 0 to 2, more preferably 0 to 0.5, k=0.05 to 1.5, preferably 0.1 to 1.0, more preferably 0.1 to 0.7, m=0 to 1, preferably 0 to 0.5, more preferably 0 to 0.1, x=0 to 3, preferably 0 to 2, more preferably 0 to 1, y=0 to 1, preferably 0 to 0.5, more preferably 0 to 0.1; i is a number of oxygen in a metal oxide formed by bonding of said respective components; and j=20 to 200, preferably 25 to 150, more preferably 30 to 100; and a number of Mo/Me is from 0.8 to 1, wherein the Mo/Me is a number obtained by dividing the product, which is 20, of a valence number of molybdenum as molybdic acid and an atomic ratio of molybdenum by the sum of respective products of respective valence numbers and atomic ratios of bismuth, iron, nickel, chromium, potassium, the F component element, the G component element and the Y component element.

Embodiments of the present invention are explained in more detail as follows.

Molybdenum, bismuth, iron, nickel, chromium, the F component element, potassium, and silica ($SiO_2$) are essential components, and if these components are not used in the above-defined composition range, the objects of the present invention cannot be accomplished. According to the present invention, a superior catalyst efficiency can be exhibited within a composition region wherein bismuth is relatively little in comparison with molybdenum. Generally speaking, in the case where the iron component is little, an acrylonitrile selectivity increases at an early stage of the reaction, but long-term stability tends to deteriorate. While, according to the catalyst composition and the ammoxidation reaction in accordance with the present invention, a superior catalyst efficiency can be steadily maintained for a long period of time. Nickel serves for stability of the catalyst structure. Potassium serves to control acidity of the catalyst, and acts to improve the acrylonitrile selectivity and to prevent production of by-products. Further, both chromium and the F component, particularly preferably chromium and lanthanum and/or cerium are present at the same time. These come into effect synergistically and therefore, a specific effect cannot be expected when only chromium or only the F component, for example, only lanthanum and/or cerium is used. When both of them exist at the same time, the yield of the desired product can be improved. By the addition of chromium, an ammonia combustibility decreases and production of by-products decreases. The addition amounts of these components are important, and if any is beyond the range defined above, the effects remarkably decrease.

With respect to the catalyst components, the above-mentioned antimony and the G, H, M, X and Y components may be additionally incorporated. As the case may be, these components are added for the purpose of stabilization of the catalyst structure, improvement of oxidation reduction characteristics, control of acidity and basicity and others. As the G component, magnesium, calcium, manganese, cobalt and zinc etc. are preferred, and as the H component, zirconium, vanadium, niobium, tungsten and germanium etc. are preferred. If desired, the X component may be incorporated in a small amount for the purpose of improving the acrylonitrile selectivity or others. As the Y component, rubidium and cesium are preferred.

The present invention presupposes a fluidized bed reaction. Accordingly, the catalyst is additionally required to have physical properties suitable for the fluidized bed reaction. That is, it is additionally required that its bulk density, particle strength, attrition resistance, specific surface area, fluidity and others are suitable. For that purpose, silica is used as a carrier component.

In blending the metal molybdate-producible metal elements, that is, bismuth, iron, nickel, chromium, potassium, the F component element material and the molybdenum component material, and if desired, the G and Y component element materials, it is important that the number obtained by dividing Mo by Me, namely Mo/Me, is taken as 0.8 to 1, provided that the valence numbers of nickel and the G component are assigned to be 2, respectively, those of bismuth, iron, chromium and the F component are assigned to be 3, respectively, those of potassium and the Y component are assigned to be 1, respectively, the product (Mo) of the valence number (2) of molybdenum as molybdic acid ($(MoO_4)^{2-}$) and the atomic ratio thereof (10) is 20 (=2×10), and the sum of respective products of respective valence numbers and atomic ratios of bismuth, iron, nickel, chromium, potassium, and the F, G and Y component elements is Me (: 3a+3b+2d+3e+3f+2g+k+y). This is extremely important for obtaining a superior catalyst structure in a composition region where bismuth is little. This kind of the catalyst is composed of multiple layers, which have to be systemically related to one another. However, when the Mo/Me ratio is less than 0.8, the metal elements, which are to be counter ions of the molybdic acid, do not form their molybdates, but only their oxides or others, and as a result, it is easy to deteriorate selectivity of the desired product in the catalytic reaction. It is finding that it is difficult to obtain a satisfactory relation between said multiple layers in a composition region where the Mo/Me ratio exceeds 1. It seems that this is one of reasons why the repeatability in the production of the catalyst deteriorates in a conventional composition region. It also seems that when the ratio exceeds 1, the free molybdenum is converted into its oxide, which enters between the layers to cause inhibition of the catalytic function. For preparing the catalyst in accordance with the present invention, it is allowed to select a process to be applied from processes disclosed in the above-mentioned prior arts. Particularly preferably, it is recommendable to apply the process according to Japanese Patent Nos. 2640356 and 2747920.

Materials used for the molybdenum component include molybdenum oxide and ammonium paramolybdate, wherein ammonium paramolybdate is preferably used. Materials used for the bismuth component include bismuth oxide, bismuth nitrate, bismuth carbonate and bismuth oxalate, wherein bismuth nitrate is preferably used. Materials used for the iron component include iron nitrate such as ferrous nitrate (iron (II) nitrate) and ferric nitrate (iron (III) nitrate), and iron oxalate such as ferrous oxalate (iron (II) oxalate) and ferric oxalate (iron (III) oxalate), wherein preferred is the iron nitrate. Materials used for the nickel component include nickel nitrate, nickel hydroxide and nickel oxide, wherein nickel nitrate is preferably used, and materials used for the chromium component include chromium nitrate, chromium oxide and anhydrous chromic acid, wherein chromium nitrate is preferably used. Materials of the F component include respective nitrates, oxides and hydroxides, preferably nitrates. Materials used for the potassium component include potassium nitrate and potassium hydroxide, wherein potassium nitrate is preferably used. Materials used for the antimony component include antimony trioxide, antimony pentoxide and iron antimonate, and materials of the G component include respective oxides, hydroxides and nitrates. Materials of the H component include respective oxides, and oxygen acids and their salts. Materials of the M component include respective oxides, oxygen acids and their salts, hydroxides and nitrates. With respect to the X component, materials used for boron include boric acid and anhydrous boric acid, wherein anhydrous boric acid is preferably used, materials used for phosphorus include phosphoric acid such as orthophosphoric acid, and materials used for tellurium include metal tellurium, tellurium dioxide, tellurium trioxide and telluric acid. Materials of the Y component include respective nitrates and hydroxides. Materials used for silica include silica sol and fumed silica. It is convenient to use silica sol.

These catalyst materials are blended, and thereafter the resulting blend is subjected to spray drying and calcination, thereby to obtain a desired fluidized bed catalyst. The catalyst-materials are blended and, if necessary pH of the slurry was adjusted, and the resulting slurry is subjected to heat treatment and others thereby to be able to prepare a catalyst slurry. In preparing the catalyst slurry, preparation conditions such as a mixing means of the materials, temperature, pressure and atmosphere can be voluntarily determined. A process according to that disclosed in Japanese Patent No. 2640356 can be given as a particularly preferred process. When the process is accompanied with a procedure of adjusting the pH to a relatively high degree, it is recommendable to apply a process according to that disclosed in Japanese Patent No. 2747920. That is, a chelating agent such as ethylenediamine tetraacetate, lactic acid, citric acid, tartaric acid and gluconic acid is added to coexist in the above-mentioned catalyst slurry, thereby preventing the slurry from gelling. Such a chelating agent may exhibit any effect when used in a small amount even in the case where the pH adjusted is relatively low such as 1 to 3. It is also finding that viscosity of the slurry can be lowered to improve operation of the catalyst production when the chromium component exists and when the process is accompanied with a procedure of adjusting the pH to a relatively high degree. Particularly when the pH is adjusted to from 3 to 8, the yield of the desired product may increase or combustibility of ammonia may decrease.

The thus prepared slurry can be dried by means of spray drying. A spray drying apparatus is not particularly limited, and may be a conventional one such as a rotary-disk type and a nozzle type. A slurry concentration of the slurry entering the spray drying apparatus is preferably from about 10 to about 40% by weight in terms of an oxide of the element constituting the catalyst. The catalyst materials can be granulated by means of the spray drying. A spray drying temperature is not particularly limited. In carrying out the spray drying, pressure and atmosphere can be voluntarily determined. These spray-drying conditions are determined so as to obtain a catalyst having a desired particle diameter as a fluidized bed catalyst.

After completion of the drying, calcination can be carried out to obtain a desired fluidized bed catalyst. In carrying out the calcination, calcination conditions such as a calcination means, temperature, pressure and atmosphere can be voluntarily determined. For example, the calcination can be carried out at 200 to 500° C., and additionally at 500 to 700° C. for 0.1 to 20 hours. A calcination atmosphere is preferably an oxygen containing gas. It is conveniently carried-out in air, which may be used in combination with a combination of oxygen and nitrogen, carbonic acid gas, water vapor or the like. For the calcination, a box type calciner, a tunnel type calciner, a rotary calciner, a fluidized bed calciner and others can be used. It is recommendable to adjust a particle diameter of the thus obtained fluidized bed catalyst to preferably from 5 to 200 $\mu$m, more preferably from 20 to 150 $\mu$m. Incidentally, the particle diameter used herein is not an average particle diameter of the whole particles, but a particle diameter of the individual particles.

In using a catalyst containing molybdenum as a main component for the production of acrylonitrile, as mentioned above, it is known that the molybdenum-containing material is added during the reaction, thereby maintaining the yield of the desired product. However, such an effect cannot be expected to a sufficient extent unless such a process is applied to a catalyst having a stable catalyst structure. Since the catalyst in accordance with the present invention is relatively structurally stable even when used for a long period of time at a temperature exceeding 400° C., at which this kind of the ammoxidation reaction is carried out, the reaction can be continued while adding the molybdenum-containing material, thereby maintaining the yield of desired products equal or superior to those of the early stage. However, even when such a structurally stable catalyst is used, the molybdenum component evaporates little by little from the catalyst under a reaction condition, and maybe this causes damage of the structure of metal molybdate. Accordingly, when the molybdenum-containing material is supplied, it is necessary that the molybdenum-containing material be supplied before it becomes impossible to restore such a damage of the metal molybdate structure.

The molybdenum-containing material used here includes metal molybdenum, molybdenum trioxide, molybdic acid, ammonium dimolybdate, ammonium paramolybdate, ammonium octamolybdate, ammonium dodecamolybdate, phosphomolybdic acid, and those obtained by supporting these molybdenum-containing materials with an inert substance or the above-mentioned catalyst. Of these, preferred are molybdenum trioxide, ammonium paramolybdate and those obtained by supporting these molybdenum-containing materials with an inert substance or the above-mentioned catalyst. Although the molybdenum-containing material can be used in a gaseous state or a liquid state, it is preferred from a practical point of view that these solid molybdenum-containing materials are used in a powder state. It is particularly effective to apply a process comprising using a molybdenum-enriched catalyst obtained by enriching the above-mentioned catalyst with the molybdenum-containing material. According to the process, molybdenum in the molybdenum-containing material added can be efficiently utilized, and troubles caused by precipitation of the molybdenum oxide in the system or other reasons can be avoided. For preparing the molybdenum-enriched catalyst, the process described in JP-A-11-33400 or the like can be applied.

These molybdenum-containing materials may be added in a reactor in a continuous or intermittent manner at intervals. The time of addition and an amount to be added may be appropriately determined depending upon the yield of desired products. The amount added at a time is preferably from 0.01 to 3% by weight, more preferably from 0.05 to 2% by weight, as molybdenum element based on the weight of the catalyst filled in a reactor. It is necessary to pay attention to the followings. When the molybdenum-containing material is added in a large amount in a time, it may happen that the substance wastefully escapes out of the reaction system, thereby resulting in useless consumption, and moreover the material precipitates or accumulates inside of the reactor to cause operational problems.

The ammoxidation of propylene is usually carried out at a reaction temperature of 370 to 500° C. under a reaction pressure of from atmospheric-pressure to 500 kPa using a feeding gas-having a composition of propylene/ammonia/oxygen=1/0.9 to 1.3/1.6 to 2.5 (molar ratio). An apparent contact time is usually from 0.1 to 20 seconds. It is convenient to use air as an oxygen source, which air may be diluted with water vapor, nitrogen, carbonic acid gas, a saturated hydrocarbon or the like, or may be enriched with oxygen.

BEST MODE FOR CARRYING OUT INVENTION

The present invention is explained in more detail with reference to Examples and Comparative Examples, which are not intended to limit the scope of the present invention.

DETERMINATION OF CATALYST ACTIVITY

Synthesis of acrylonitrile by means of ammoxidation of propylene was carried out as follows to evaluate the catalyst activity.

A catalyst was filled in a fluidized bed reactor having a catalyst fluidizing zone of an inner diameter of 25 mm and a height of 400 mm, and a mixed gas having a composition of propylene/ammonia/air/water vapor=1/1.2/9.5/0.5 (molar ratio) was introduced therein at a linear velocity of the gaseous feedstock of 4.5 cm/sec. The reaction pressure was controlled to 200 kPa.

Still, at the time of reaction, a molybdenum-containing material was appropriately added. The molybdenum-containing material such as some molybdenum compounds and molybdenum component-enriched catalysts was added, at intervals of 100 to 500 hours, in an amount of 0.1 to 0.2% by weight as molybdenum element based on the weight of the catalyst filled. The molybdenum-containing material, which was in a powder state, was fed from an upper part of a reactor.

Contact time and the acrylonitrile yield were found according to the following calculation equations, respectively.

Contact time (sec)=Volume of catalyst (ml) based on apparent bulk density/Flow rate of feeding gas converted to reaction conditions (ml/sec)

Acrylonitrile yield (%)=Mole number of acrylonitrile produced/Mole number of propylene supplied×100

EXAMPLE 1

A catalyst of a composition, $Mo_{10} Bi_{0.4} Fe_{1.3} Ni_6 Cr_{0.8} Ce_{0.4} K_{0.2} P_{0.2} B_{0.2} O_i (SiO_2)_{35}$ (i is a number naturally determined depending upon the valence numbers of the other elements), was prepared as follows.

In 3000 g of pure water, 346.5 g of ammonium paramolybdate was dissolved, and successively 4.5 g of 85% phosphoric acid and 1.4 g of anhydrous boric acid were independently added thereto. The resulting liquid was mixed with a liquid obtained by dissolving 38.1 g of bismuth nitrate, 4.0 g of potassium nitrate, 342.5 g of nickel nitrate, 62.8 g of chromium nitrate, 34.1 g of cerium nitrate and 25.0 g of citric acid in 270 g of 3.3% nitric acid. Another liquid obtained by dissolving 103.1 g of ferric nitrate and 25.0 g of citric acid in 270 g of pure water was prepared and added to the above mixture. Successively, 2064.0 g of 20% silica sol was added thereto. The resulting slurry was adjusted to pH 2 by addition of 15% aqueous ammonia while being stirred, and subjected to heat treatment at 98° C. for 1.5 hours.

The thus prepared slurry was spray dried using a rotary disk type spray drier, whose inlet temperature and outlet temperature were controlled to 330° C. and 160° C., respectively. The dried Particle was subjected to heat treatment at 250° C. for 2 hours and additionally at 400° C. for 2 hours, and finally subjected to fluidized calcination at 660° C. for 3 hours.

EXAMPLE 2

A catalyst having a composition of $Mo_{10} Bi_{0.4} Fe_{1.1} Ni_{4.0} Cr_{0.8} CO_{2.0} Ce_{0.5} K_{0.3} P_{0.2} O_i (SiO_2)_{35}$ was prepared in a manner similar to that of Example 1, and then subjected to calcination under conditions as shown in Table 1, except that no anhydrous boric acid was added and cobalt nitrate as a Co material additionally dissolved in the above-mentioned nitric acid was added.

EXAMPLE 3

A catalyst having a composition of $Mo_{10} Bi_{0.4} Fe_{1.3} K_{0.2} Ni_{5.5} Zn_{0.2} Cr_{1.5} Ce_{0.6} La_{0.2} Ge_{0.2} B_{0.2} O_i (SiO_2)_{35}$ was prepared in a manner similar to that of Example 1, and then subjected to calcination under conditions as shown in Table 1, except that no phosphoric acid was added, and both lanthanum nitrate and zinc nitrate as a La material and a Zn material, respectively, additionally dissolved in the above-mentioned nitric acid, and germanium oxide as a Ge material were independently added next to the addition of ammonium paramolybdate.

EXAMPLE 4

A catalyst having a composition of $Mo_{10} Bi_{0.3} Fe_{1.5} K_{0.2} Ni_5 Mg_1 Cr_{0.5} Ce_{0.3} Pr_{0.2} O_i (SiO_2)_{35}$ was prepared in a manner similar to that of Example 1, and then subjected to calcination under conditions as shown in Table 1, except that phosphoric acid and anhydrous boric acid were not added, and praseodymium nitrate and magnesium nitrate as a Pr material and an Mg material, respectively, additionally dissolved in the above-mentioned nitric acid were added.

EXAMPLE 5

A catalyst having a composition of $Mo_{10} Bi_{0.5} Fe_{1.3} K_{0.1} Ni_{5.75} Mn_{0.5} Cr_{0.8} Ce_{0.75} Pd_{0.01} Rb_{0.1} P_{0.1} B_{0.1} O_i (SiO_2)_{40}$ was prepared as follows.

In 3000 g of pure water, 321.1 g of ammonium paramolybdate was dissolved, and successively 2.1 g of 85% phosphoric acid and 0.6 g of anhydrous boric acid were added thereto. The resulting liquid was mixed with a liquid obtained by dissolving 44.1 g of bismuth nitrate, 1.8 g of potassium nitrate, 304.1 g of nickel nitrate, 26.1 g of manganese nitrate, 58.2 g of chromium nitrate, 59.2 g of cerium nitrate, 0.4 g of palladium nitrate, 2.7 g of rubidium nitrate and 25 g of citric acid in 270 g of 3.3% nitric acid. Successively, 2185.5 g of 20% silica sol was added thereto. Thereafter, the resulting mixture was adjusted to pH 7.7 by dropwise-addition of 15% aqueous ammonia while being stirred, and subjected to heat treatment at 98° C. for 1.5 hours. In 270 g of pure water, 95.5 g of ferric nitrate and 25 g of citric acid were dissolved to prepare a liquid.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 670° C. for 3 hours. EXAMPLE 6

A catalyst having a composition of $Mo_{10} Bi_{0.8} Fe_{1.3} K_{0.2} Ni_{5.5} Cr_{0.8} Ce_{0.4} W_{0.5} P_{0.2} O_i (SiO_2)_{60}$ was prepared as follows.

In 3000 g of pure water, 19.2 g of ammonium paratungstate was dissolved, and thereafter 260 g of ammonium paramolybdate was dissolved therein, and furhter 3.4 g of 85% phosphoric acid was added thereto. The resulting liquid was mixed with a liquid obtained by dissolving 57.2 g of bismuth nitrate, 3.0 g of potassium nitrate, 235.6 g of nickel nitrate, 47.1 g of chromium nitrate, 25.6 g of cerium nitrate and 25 g of citric acid in 270 g of 3.3% nitric acid. Successively, 2655.1 g of 20% silica sol was added thereto. The resulting slurry was adjusted to pH 5 by dropwise-addition of 15% aqueous ammonia while being stirred, and subjected to heat treatment under reflux at 98° C. for 1.5 hours. A liquid prepared by dissolving 77.4 g of ferric nitrate and 25 g of citric acid in 270 g of pure water was added thereto.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 670° C. for 3 hours.

EXAMPLE 7

A catalyst having a composition of $Mo_{10}$ $Bi_{0.5}$ $Fe_2$ $K_{0.2}$ $Ni_4$ $Mg_{1.5}$ $Cr_{0.5}$ $Ce_{0.5}$ $Al_{0.1}$ $Oi$ $(SiO_2)_{35}$ was prepared in a manner similar to that of Example 6, and then subjected to calcination under conditions as shown in Table 1, except that ammonium paratungstate and phosphoric acid were not added, and aluminum nitrate and magnesium nitrate as an Al material and an Mg material, respectively, additionally dissolved in the above-mentioned nitric acid, and niobium hydrogen oxalate as an Nb material were independently added next to the addition of ammonium paramolybdate.

EXAMPLE 8

A catalyst having a composition of $Mo_{10}$ $Bi_{0.5}$ $Fe_1$ $Sb_1$ $K_{0.2}$ $Ni_4$ $Co_{1.5}$ $Cr_2$ $Ce_{0.5}$ $Ru_{0.05}$ $Cs_{0.05}$ $P_{0.3}$ $Oi$ $(SiO2)_{35}$ was prepared in a manner similar to that of Example 6, and then subjected to calcination under conditions as shown in Table 1, except that no ammonium paratungstate was added, and cobalt nitrate and cesium nitrate as a Co material and a Cs material, respectively, additionally dissolved in the above-mentioned nitric acid, and antimony tetroxide and ruthenium oxide as an Sb material and an Ru material, respectively, were independently added next to the addition of ammonium paramolybdate.

EXAMPLE 9

A catalyst having a composition of $Mo_{10}$ $Bi_{0.5}$ $Fe_{1.3}$ $Sb_5$ $K_{0.2}$ $Ni_6$ $Cr_1$ $Ce_{0.2}$ $Nd_{0.2}$ $Zr_{0.2}$ $P_{0.1}$ $Oi$ $(SiO_2)_{35}$ was prepared in a manner similar to that of Example 6, and then subjected to calcination under conditions as shown in Table 1, except that no ammonium paratungstate was added, and neodymium nitrate and zirconium oxynitrate as an Nd material and a Zr material, respectively, additionally dissolved in the above-mentioned nitric acid, and antimony tetroxide as an Sb material were independently added next to the addition of ammonium paramolybdate.

EXAMPLE 10

A catalyst having a composition of $Mo_{10}$ $Bi_{0.5}$ $Fe_{1.2}$ $Sb_{10}$ $K_{0.2}$ $Ni_{5.75}$ $Cr_{1.5}$ $Ce_{0.5}$ $Sm_{0.2}$ $V_{0.1}$ $Te_{0.25}$ $Oi$ $(SiO_2)_{35}$ was prepared in a manner similar to that of Example 6, and then subjected to calcination under conditions as shown in Table 1, except that ammonium paratungstate and phosphoric acid were not added, and samarium nitrate as an Sm material additionally dissolved in the above-mentioned nitric acid, ammonium methavanadate as a V material and antimony tetroxide as an Sb material were independently added next to the addition of ammonium paramolybdate, and moreover a liquid obtained by dissolving telluric acid as a Te material in water was added to the solution of ferric nitrate and citric acid.

Comparative Example 1

A catalyst having a composition of $Mo_{10}$ $Bi_{0.4}$ $Fe_{0.6}$ $K_{0.2}$ $Ni_6$ $Cr_{0.8}$ $Ce_{0.4}$ $P_{0.2}$ $B_{0.2}$ $Oi$ $(SiO_2)_{35}$ was prepared in a manner similar to that of Example 1, and then subjected to calcination under conditions as shown in Table 1, except that the amount of ferric nitrate was changed.

Comparative Example 2

A catalyst having a composition of $Mo_{10}$ $Bi_{0.4}$ $Fe_{1.1}$ $K_{0.2}$ $Ni_6$ $P_{0.2}$ $B_{0.2}$ $Oi$ $(SiO_2)_{35}$ was prepared in a manner similar to that of Example 1, and then subjected to calcination under conditions as shown in Table 1, except that chromium nitrate and cerium nitrate were not added.

Comparative Example 3

A catalyst having a composition of $Mo_{10}$ $Bi_1$ $Fe_{1.3}$ $K_{0.2}$ $Ni_{5.5}$ $Zn_{0.2}$ $Cr_{1.5}$ $Ce_{0.6}$ $La_{0.2}$ $Ge_{0.2}$ $B_{0.2}$ $Oi$ $(SiO_2)_{35}$ was prepared in a manner similar to that of Example 6, and then subjected to calcination under conditions as shown in Table 1, except that ammonium paratungstate and phosphoric acid were not added, and lanthanum nitrate and zinc nitrate as a La material and a Zn material, respectively additionally dissolved in the above-mentioned nitric acid, anhydrous boric acid as a B material and germanium oxide as a Ge material were independently added next to the addition of ammonium paramolybdate.

Comparative Example 4

A catalyst having a composition of $Mo_{10}$ $Bi_{0.4}$ $Fe_2$ $K_{0.2}$ $Ni_6$ $Zn_{0.2}$ $Cr_{1.5}$ $Ce_{0.6}$ $La_{0.2}$ $Ge_{0.2}$ $B_{0.2}$ $Oi$ $(SiO_2)_{35}$ was prepared in a manner similar to that of Example 6, and then subjected to calcination under conditions as shown in Table 1, except that ammonium paratungstate and phosphoric acid were not added, and lanthanum nitrate and zinc nitrate as a La material and a Zn material, respectively, additionally dissolved in the above-mentioned nitric acid, anhydrous boric acid as a B material and germanium oxide as a Ge material were independently added next to the addition of ammonium paramolybdate.

Incidentally, the molybdenum-enriched catalysts used for the ammoxidation reaction in Examples 3 and 7 to 10 and Comparative Examples 3 and 4 were those prepared by impregnating the catalysts obtained in the corresponding Examples and Comparative Examples with an aqueous solution of ammonium paramolybdate, followed by drying and calcination.

Using the catalysts obtained in these Examples and Comparative Examples, the ammoxidation reaction of propylene was carried out under the foregoing conditions. The results were as shown in the following Table.

TABLE 1

| | Catalyst composition (atomic ratio) | | | | | | | | | | | | | | | |
|---|---|---|---|---|---|---|---|---|---|---|---|---|---|---|---|---|
| | Mo | Bi | Fe | Sb | Ni | Cr | F | G | H | K | M | X | Y | SiO₂ | Mo/Me |
| Example | | | | | | | | | | | | | | | |
| 1 | 10 | 0.4 | 1.3 | | 6 | 0.8 | Ce 0.4 | | | 0.2 | | P 0.2 | B 0.2 | 35 | 0.96 |
| 2 | 10 | 0.4 | 1.1 | | 4 | 0.8 | Ce 0.5 | | Co 2 | 0.3 | | P 0.2 | | 35 | 0.97 |
| 3 | 10 | 0.4 | 1.3 | | 5.5 | 1.5 | Ce 0.6 | La 0.2 | Zn 0.2 | Ge 0.2 | 0.2 | B 0.2 | | 35 | 0.85 |
| 4 | 10 | 0.3 | 1.5 | | 5 | 0.5 | Ce 0.3 | Pr 0.2 | Mg 1 | | 0.2 | | | 35 | 0.97 |
| 5 | 10 | 0.5 | 1.3 | | 5.75 | 0.8 | Ce 0.75 | | Mn 0.5 | | 0.1 | Pd 0.01 | P 0.1 | B 0.1 | Rb 0.1 | 40 | 0.88 |
| 6 | 10 | 0.8 | 1.3 | | 5.5 | 0.8 | Ce 0.4 | | W 0.5 | | 0.2 | | P 0.2 | | 60 | 0.95 |
| 7 | 10 | 0.5 | 2 | | 4 | 0.5 | Ce 0.5 | Al 0.1 | Mg 1.5 | Nb 0.1 | 0.2 | | | | 35 | 0.91 |
| 8 | 10 | 0.5 | 1 | 1 | 4 | 2 | Ce 0.5 | | Co 1.5 | | 0.2 | Ru 0.05 | P 0.3 | Cs 0.05 | 35 | 0.86 |
| 9 | 10 | 0.5 | 1.3 | 5 | 6 | 1.0 | Ce 0.2 | Nd 0.2 | | Zr 0.2 | 0.2 | | P 0.1 | | 35 | 0.92 |
| 10 | 10 | 0.5 | 1.2 | 10 | 5.75 | 1.5 | Ce 0.5 | Sm 0.2 | V 0.1 | | 0.2 | Te 0.25 | | | 35 | 0.85 |
| Comparative Example | | | | | | | | | | | | | | | |
| 1 | 10 | 0.4 | 0.6 | | 6 | 0.8 | Ce 0.4 | | | | 0.2 | | P 0.2 | B 0.2 | 35 | 1.06 |
| 2 | 10 | 0.4 | 1.1 | | 6 | | | | | | 0.2 | | P 0.2 | B 0.2 | 35 | 1.20 |
| 3 | 10 | 1 | 1.3 | | 5.5 | 1.5 | Ce 0.6 | La 0.2 | Zn 0.2 | Ge 0.2 | 0.2 | | B 0.2 | | 35 | 0.78 |
| 4 | 10 | 0.4 | 2 | | 6 | 1.5 | Ce 0.6 | La 0.2 | Zn 0.2 | Ge 0.2 | 0.2 | | B 0.2 | | 35 | 0.75 |

| | Calcination conditions | | Reaction conditions | | Acrylonitrile yield [%] | | | Kind of Molybdenum added |
|---|---|---|---|---|---|---|---|---|
| | Temperature [° C.] | Time [hr] | Temperature [° C.] | Contact time [sec] | Time elapsed [hr] | | | |
| | | | | | 50 | 500 | 1000 | |
| Example | | | | | | | | |
| 1 | 660 | 3 | 440 | 3.0 | 81.7 | 81.8 | 81.7 | Ammonium paramolydate |
| 2 | 640 | 3 | 440 | 3.0 | 81.9 | 81.9 | 81.7 | Molybdenum trioxide |
| 3 | 670 | 3 | 440 | 3.2 | 81.4 | 81.5 | 81.3 | Molybdenum-enriched catalyst |
| 4 | 650 | 3 | 440 | 3.0 | 81.6 | 81.5 | 81.4 | Molybdenum trioxide |
| 5 | 670 | 3 | 440 | 3.5 | 81.2 | 81.0 | 80.9 | Ammonium paramolybdate |
| 6 | 670 | 3 | 440 | 3.2 | 81.3 | 81.3 | 81.2 | Ammonium paramolybdate |
| 7 | 630 | 3 | 440 | 3.2 | 81 | 81.2 | 81.1 | Molybdenum-enriched catalyst |
| 8 | 610 | 3 | 440 | 3.0 | 81.5 | 81.3 | 81.4 | Molybdenum-enriched catalyst |
| 9 | 670 | 3 | 440 | 3.5 | 81.4 | 81.2 | 81.2 | Molybdenum-enriched catalyst |
| 10 | 680 | 3 | 440 | 3.7 | 81.8 | 81.9 | 81.6 | Molybdenum-enriched catalyst |
| Comparative Example | | | | | | | | |
| 1 | 640 | 3 | 440 | 3.0 | 81.6 | 80.5 | 79.2 | Ammonium paramolybdate |
| 2 | 650 | 3 | 440 | 3.2 | 80.5 | 80.2 | 78.8 | Ammonium paramolybdate |
| 3 | 670 | 3 | 440 | 3.0 | 80.8 | 80.3 | 78.5 | Molybdenum-enriched catalyst |
| 4 | 690 | 3 | 440 | 3.5 | 81.2 | 80.1 | 78.6 | Molybdenum-enriched catalyst |

INDUSTRIAL APPLICABILITY

The process for producing acrylonitrile in accordance with the present invention can give a high acrylonitrile yield. Moreover, it is possible to increase long-term stability of the reaction owing to a stable catalyst structure, and to maintain the catalyst efficiency for a long period of time by adding and supplying a molybdenum component.

What is claimed is:

1. A process for producing acrylonitrile, comprising:
carrying out the ammoxidation of propylene in the presence of a fluidized bed catalyst having a composition represented by the following empirical formula:

$$Mo_{10} Bi_a Fe_b Sb_c Ni_d Cr_e F_f G_g H_h K_k M_m X_x Y_y O_i (SiO2)_j$$

wherein Mo, Bi, Fe, Sb, Ni, Cr and K are molybdenum, bismuth, iron, antimony, nickel, chromium and potassium, respectively; F is at least one element selected from the group consisting of yttrium, lanthanum, cerium, praseodymium, neodymium, samarium, aluminum and gallium and comprises at least lanthanum and/or cerium; G is at least one element selected from the group consisting of magnesium, calcium, strontium, barium, manganese, cobalt, copper, zinc and cadmium; H is at least one element selected from the group consisting of titanium, zirconium, vanadium, niobium, tantalum, tungsten, germanium, tin and lead; M is at least one element selected from the group consisting of ruthenium, rhodium, palladium, rhenium, osmium, iridium, platinum and silver; X is at least one element selected from the group consisting of phosphorus, boron and tellurium; Y is at least one element selected from the group consisting of lithium, sodium, rubidium, cesium and thallium; O is oxygen; Si is silicon; subscripts a, b, c, d, e, f, g, h, k, x, y, i and j are independently of one another an atomic ratio, provided that a=0.2 to 1.5, b=0.7 to 15, c=0 to 20, d=3 to 8, e=0.1 to 2.5, f=0.1 to 1.5, g=0 to 5, h=0 to 3, k=0.05 to 1.5, m=0 to 1, x=0 to 3, y=0 to 1; i is a number of oxygen in a metal oxide formed by bonding of said respective components; and j=20 to 200; and Mo/Me is from 0.8 to 1, wherein the Mo/Me is a number obtained by dividing the product, which is 20, of a valence number of molybdenum as molybdic acid and an atomic ratio of molybdenum by the sum of respective products of respective valence numbers and atomic ratios of bismuth, iron, nickel, chromium, potassium, the F component element, the G component element and the Y component element, and adding a molybdenum-containing material during said ammoxidation.

2. The process for producing acrylonitrile according to claim 1, wherein the molybdenum-containing material is a molybdenum-enriched catalyst prepared by enriching said fluidized bed catalyst with molybdenum.

3. The process according to claim 1, wherein F is one or more element which contains at least lanthanum and/or cerium and is at least one element selected from the group consisting of lanthanum, cerium, praseodymium, neodymium, samarium and aluminum; G is at least one element selected from the group consisting of magnesium, calcium, manganese, cobalt and zinc; H is at least one element selected from the group consisting of zirconium, vanadium, niobium, tungsten and germanium; M is at least one element selected from the group consisting of ruthenium and palladium; Y is at least one element selected from the group consisting of rubidium and cesium; a=0.3 to 1.2, b=0.8 to 13, c=0 to 15, d=4 to 7, e=0.2 to 2, f=0.2 to 1, g=0 to 3, h=0 to 2, k=0.1 to 1.0, m=0 to 0.5, x=0 to 2, y=0 to 0.5, and j=25 to 150.

4. The process according to claim 1, wherein the molybdenum-containing material is added in an amount of from 0.05 to 2% by weight as elemental molybdenum based on the weight of said fluidized bed catalyst.

5. The process according to claim 2, wherein the molybdenum-containing material is added in an amount of from 0.05 to 2% by weight as elemental molybdenum based on the weight of said fluidized bed catalyst.

6. The process according to claim 3, wherein the molybdenum-containing material is added in an amount of from 0.05 to 2% by weight as elemental molybdenum based on the weight of said fluidized bed catalyst.

7. The process according to claim 1, wherein the molybdenum-containing material comprises a material selected from the group consisting of metallic molybdenum, molybdenum trioxide, molybdic acid, ammonium molybdate, ammonium polymolybdate, ammonium octamolybdate, ammonium dodecamolybdate, phosphomolybdic acid, and any of the preceding materials supported on an inert substance.

8. The process according to claim 1, carried out at a temperature of from 370–500° C.

9. The process according to claim 2, carried out at a temperature of from 370–500° C.

10. The process according to claim 3, carried out at a temperature of from 370–500° C.

11. The process according to claim 1, carried out at a reaction pressure of from atmospheric pressure to 500 kPa.

12. The process according to claim 2, carried out at a reaction pressure of from atmospheric pressure to 500 kPa.

13. The process according to claim 3, carried out at a reaction pressure of from atmospheric pressure to 500 kPa.

14. The process according to claim 1, wherein the propylene is present in a feed gas comprising propylene, ammonia, oxygen and one or more of water vapor, nitrogen, carbonic acid gas, and a saturated hydrocarbon.

15. The process according to claim 2, wherein the propylene is present in a feed gas comprising propylene, ammonia, oxygen and one or more of water vapor, nitrogen, carbonic acid gas, and a saturated hydrocarbon.

16. The process according to claim 3, wherein the propylene is present in a feed gas comprising propylene, ammonia, oxygen and one or more of water vapor, nitrogen, carbonic acid gas, and a saturated hydrocarbon.

* * * * *

UNITED STATES PATENT AND TRADEMARK OFFICE
CERTIFICATE OF CORRECTION

PATENT NO. : 6,642,405 B1
DATED : November 4, 2003
INVENTOR(S) : Mori et al.

It is certified that error appears in the above-identified patent and that said Letters Patent is hereby corrected as shown below:

<u>Title page,</u>
Item [87], the PCT information is incorrect. Item [87] should read -- [87]  PCT Pub. No.:    WO0128984
         PCT Pub. Date:   Apr. 26, 2001 --

Signed and Sealed this

Twenty-seventh Day of January, 2004

JON W. DUDAS
*Acting Director of the United States Patent and Trademark Office*